United States Patent [19]

Stack et al.

[11] Patent Number: 5,059,211
[45] Date of Patent: Oct. 22, 1991

[54] ABSORBABLE VASCULAR STENT

[75] Inventors: Richard S. Stack, Chapel Hill; Zemaida P. Klopovic, Durham, both of N.C.

[73] Assignee: Duke University, Durham, N.C.

[21] Appl. No.: 66,345

[22] Filed: Jun. 25, 1987

[51] Int. Cl.$^5$ ............................................. A61M 29/00
[52] U.S. Cl. .................................... 606/198; 606/108; 606/154; 623/1
[58] Field of Search ............... 128/343, 334 R; 623/1; 606/151, 153–156, 191, 198, 108

[56] References Cited

U.S. PATENT DOCUMENTS

| 2,127,903 | 8/1938 | Bowen | 623/1 X |
| 3,657,744 | 4/1972 | Ersek | 128/334 R X |
| 4,655,771 | 4/1987 | Wallsten | 128/343 X |
| 4,693,249 | 9/1987 | Schenck et al. | 128/343 X |
| 4,733,665 | 3/1988 | Palmaz | 128/343 |
| 4,740,207 | 4/1988 | Kreamer | 128/344 R X |

OTHER PUBLICATIONS

Stent for Vascular Anastomosis—Trimble, M.D., p. 89.
Segmented Polyurethane; A Polyether Polymer—Boretos, vol. 2, pp. 121–130.
Rigid Porous Cardiovascular Prostheses—Wieting et al., vol. XIX, p. 553–560.
Diabetes, Mellitus and Atherosclerosis, Slavina, M.D.
Initial Events in Interactions of Blood with a Foreign Surface, Baier, pp. 191–206, vol. 3.
Radiological Follow-up of Transluminally Inserted Vascular Endoprostheses—Maass et al., Sep. 1984.
Transluminal Expandable Nitinol Coil Stent Grafting: Preliminary Report—Dotter, M.D., Apr. 1983.
Nonsurgical Placement of Arterial Endoprostheses: A New Technique Using Nitinol Wire—Cragg, M.D., Apr. 1983.
Percutaneous Arterial Grafting—Cragg, 1984.
Self-Expanding Endovascular Prosthesis: An Experimental Study, Rousseau et al.—1987, pp. 709–714.
Self-Expanding Metallic Stents for Small Vessels: An Experimental Evaluation—Durprat, M.D.—1987—pp. 469–472.
Percutaneous Endovascular Graft: Experimental Evaluation—Lawrence, M.D.—1987—pp. 357–360.
Endovascular Stent for Use in Aortic Dissection: An InVitro Experiment—Charnsangavej, M.D.—1985—pp. 323–323.
Percutaneous Endovascular Stents: An Experimental Evaluation—Wright, M.D.—1985—pp. 69–72.
Intravascular Stents to Prevent Occlusion and Restenosis ... Sigwart, Puel et al.—Mar. 19, 1987—pp. 701–706.
Intravascular Stents for Angioplasty—Schatz, M.D.—Dec. 1987—pp. 27–60.
Expandable Intraluminal Graft: A Preliminary Study—Palmaz, M.D., 1985—pp. 73–77.
Normal and Stenotic Renal Arteries: Experimental Balloon—Expandable Intraluminal Stenting—Palmaz, M.D., 1987—pp. 705–708.
Atherosclerotic Rabbit Aortas: Expandable Intraluminal Grafting—Palmaz—Windeler et al.—1986—pp. 723–726.
Expandable Intraluminal Vascular Graft: A Feasibility Study—Palmaz, Sibbitt et al.—1985—pp. 199–205.

Primary Examiner—Michael H. Thaler
Attorney, Agent, or Firm—Cushman, Darby & Cushman

[57] ABSTRACT

An absorbable stent for placement at the locus of a stenotic lesion which is flexible and compliance for safe and effective delivery to the cite of a coronary obstruction, for example, and so as to avoid arterial rupture or aneurysm formation while under continuous stress of a beating heart. The stent is expandable from a reduced diameter configuration, which facilitates delivery to the cite of a targeted arterial obstruction, to an expanded configuration when disposed within the targeted area. The stent can be carried to the cite to be treated and expanded to its supporting diameter on any suitable expandable catheter such as a mechanically expandable catheter or a catheter having an inflatable balloon. The stent is formed so as to have a wall with pores and/or holes to facilitate tissue ingrowth and encapsulation of the stent. The stent will subsequently be bioabsorbed to minimize the likelihood of embolization of the dissolved material.

7 Claims, 3 Drawing Sheets

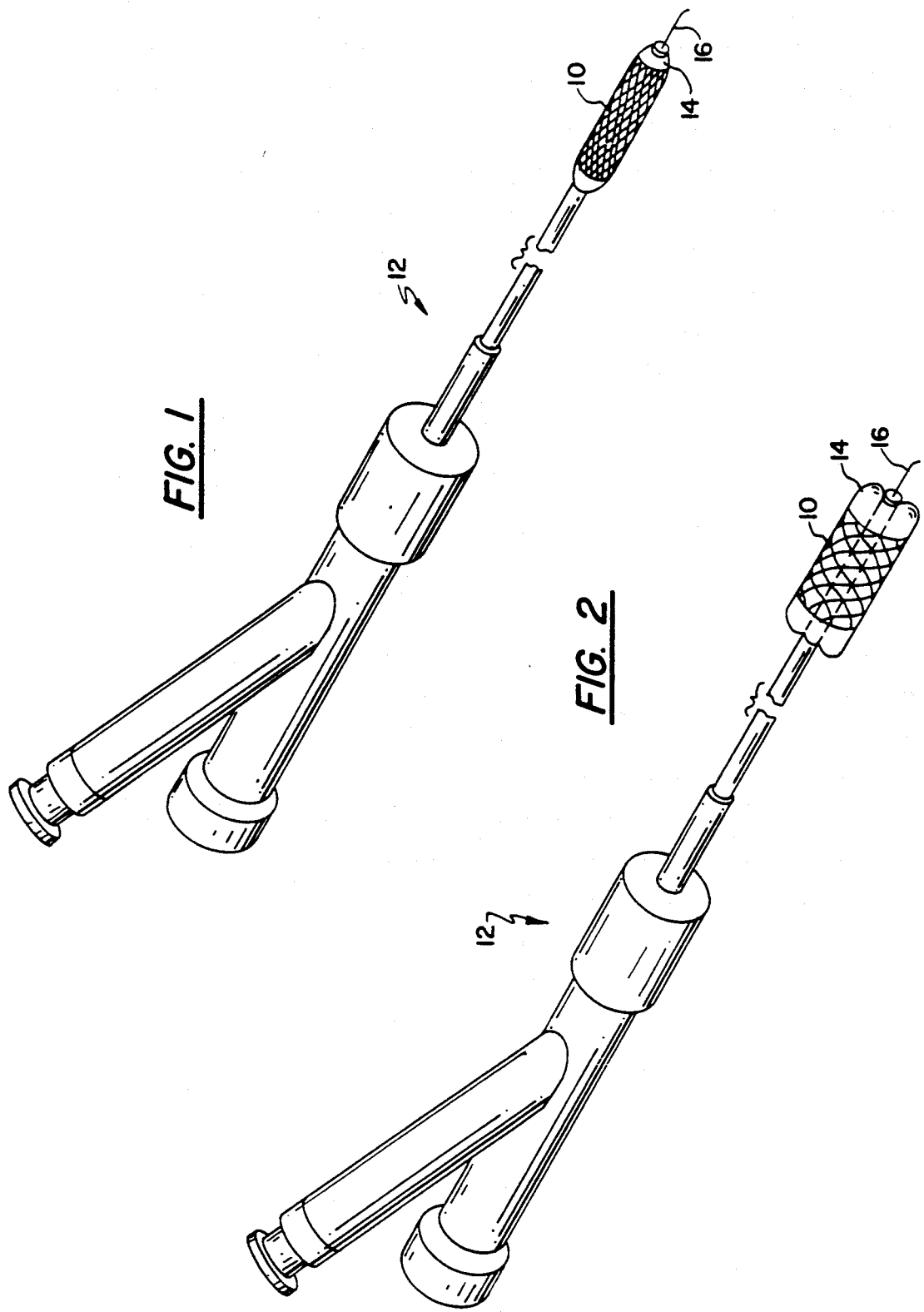

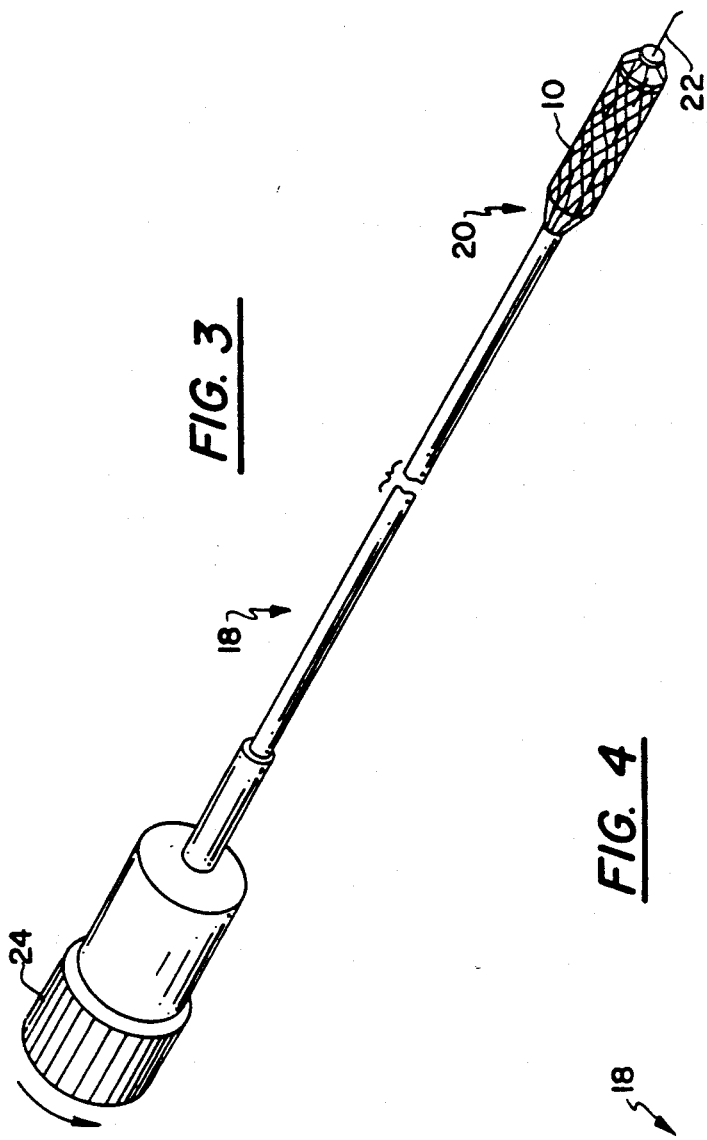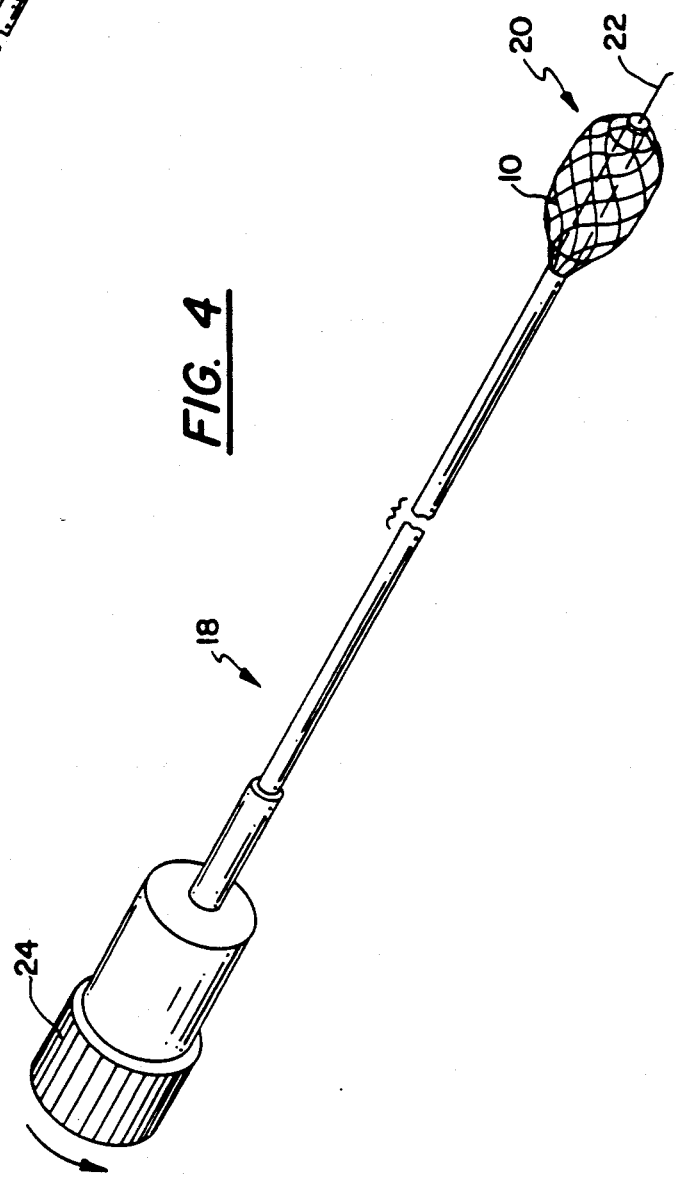

ABSORBABLE VASCULAR STENT

BACKGROUND OF THE INVENTION

This invention relates to coronary angioplasty and, more particularly, to an absorbable stent for placement within a blood vessel, such as a coronary artery, at the locus of a stenotic lesion.

A technique for coronary angioplasty has been developed which generally involves the use of a catheter system including a dilation catheter which is introduced via the femoral artery, under local anesthesia, and advanced to the site of a stenotic lesion in a coronary artery. An extensible balloon mounted on the distal end of the dilation catheter is inflated with a fluid once it is disposed within the target stenotic portion of the coronary artery. As the balloon is inflated, the atherosclerotic material in the vessel is compressed in a direction generally perpendicular to the wall of the vessel which, consequently, dilates the vessel to facilitate blood flow therethrough. While this technique has been rather successful in a number of instances, restenosis is common and, in the event the plaque cracks during expansion, subsequent collapse of the coronary artery is likely. It would therefore be desirable to minimize restenosis of the vessel by maintaining the plaque in its compressed disposition while, at the same time, preventing collapse of the vessel subsequent to plaque dilation. One manner in which the foregoing can be achieved is by placing a stent within the afflicted vessel at the locus of the stenotic lesion after the plaque has been dilated or, preferably, at the time of plaque dilation.

One such stent has been proposed and tested in Europe and described in the article of Stignart, et al. titled "Intravascular Stents to Prevent Occlusion and Restenosis after Transluminal Angioplasty", published in the *New England Journal of Medicine*, Vol. 316, No. 12, Mar. 19, 1981, pages 701–706. This stent is in the form of a "Chinese finger handcuff" metallic mesh which can be expanded and compressed in diameter. The stent is made by cutting desired lengths from an elongated tube of metal mesh and, accordingly, has the disadvantage that metal prongs from the length cutting process remain at the longitudinal ends thereof. The inherent rigidity of the metal used to form the stent together with these terminal prongs make navigation of the blood vessels to the locus of the lesion difficult as well as risky from the standpoint of injury to healthy tissue along the passage to the target vessel. Further, when this stent is permanently placed in a coronary artery, the continuous stress from the beating of the heart would cause the prongs to damage the healthy vessel walls adjacent to the lesion. This damage could lead to arterial rupture or aneurysm formation. Finally, because it is adapted to be chronically implanted within the vessel, the continued exposure of the stent to blood can lead to thrombus formation within the blood vessel with dilitarious results.

It would therefore be desirable to provide a stent that has sufficient structural integrity to be placed within a vessel at the site of a stenotic lesion to support the vessel wall against collapse and yet is flexible and compliant enough for safe and effective delivery to the site of a coronary obstruction. It would further be desirable to provide a stent which is soft and compliant enough to avoid arterial rupture or aneurysm formation at the ends of the stent even when exposed to continuous stresses from the beating heart during chronic implantation. It would also be desirable to provide a stent which avoids the limitations of chronic implantation by becoming absorbed into the vessel wall after healing of the angioplasty site. It would be further desirable to use a bioabsorbable material that could be formed in such a way, i.e., in a mesh-like or porous configuration, that will enable endothelial cells at the angioplasty site to grow into and over the stent so that bio-degradation will occur within the vessel wall rather than in the lumen which could lead to embolization of the dissolved material.

SUMMARY OF THE INVENTION

The present invention provides a stent which can support a vessel wall for a period of time following coronary angioplasty but which overcomes the drawbacks of the above-mentioned metallic stent. More particularly, the present invention is directed to an absorbable stent for placement at the locus of a stenotic lesion which is flexible and compliant for safe and effective delivery to the coronary obstruction and so as to avoid arterial rupture or aneurysm formation while under continuous stress of a beating heart. The stent formed in accordance with the present invention is expandable from a reduced diameter configuration, which facilitates delivery to the site of a targeted arterial obstruction, to an expanded configuration when disposed within the targeted area of the vessel. As such, the stent can be delivered to the locus of a lesion in its reduced diameter configuration on the distal end of an expandable catheter and can be expanded in vivo to its supporting diameter by expanding the expandable portion of its associated catheter.

A stent formed in accordance with the present invention can be carried to the site to be treated and expanded to its supporting diameter on any suitable expandable catheter. Thus, the stent can be placed on the distal balloon of a coronary balloon catheter for delivery to the treatment cite. Alternately, the stent can be placed on the distal end of a mechanically extensible catheter of the type including a rotatable knob on its proximal end which, when rotated, will effect an expansion of the catheter distal end portion so as to expand the stent mounted thereon. Further, because the stent is carried on a dilatable catheter, the plaque can be compressed at the time of stent placement.

Other objects, features, and characteristics of the present invention, as well as the methods of operation and functions of the related elements of the structure, and the combination of parts and economies of manufacture, will become more apparent upon consideration of the following description with reference to the accompanying drawings, all of which form a part of this specification.

BRIEF DESCRIPTION OF THE DRAWINGS

FIG. 1 is a perspective view of an absorbable stent formed in accordance with the present invention, in its collapsed state and mounted on a balloon catheter prior to placement in a blood vessel;

FIG. 2 is a perspective view of the assembly of FIG. 1 with the balloon of the catheter inflated so that the stent is in its expanded configuration;

FIG. 3 is a perspective view of an absorbable stent formed in accordance with the present invention, in its collapsed state and mounted on a catheter having a mechanical expansion device prior to insertion into a blood vessel;

FIG. 4 is a perspective view of the assembly of FIG. 3 with the mecanical device expanded so that the stent is in its expanded configuration;

DETAILED DESCRIPTION OF THE PRESENTLY PREFERRED EXEMPLARY EMBODIMENTS

Figure 6:
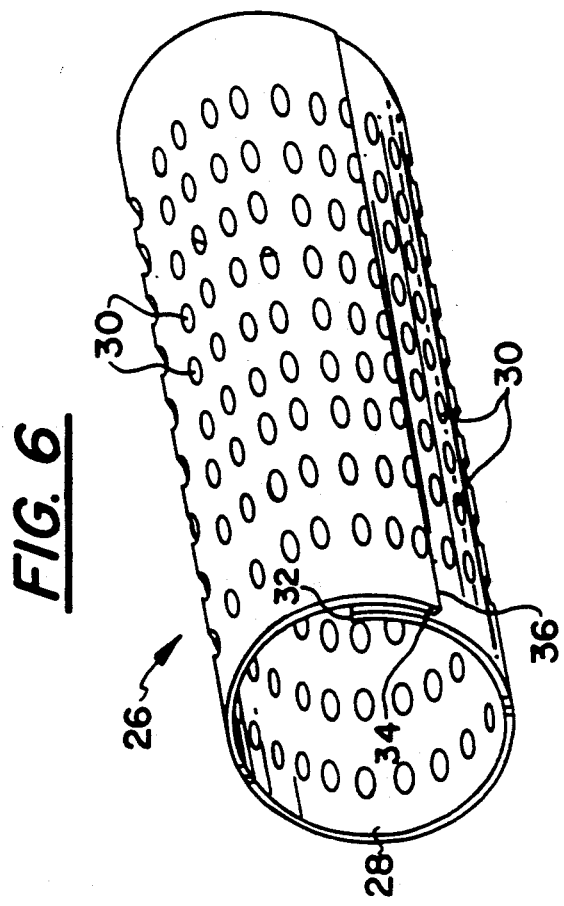
FIG. 6 is an end view of the stent of FIG. 5.

Referring in particular to FIGS. 1-2, a first embodiment of an absorbable stent formed in accordance with the present invention is shown, mounted on a suitable balloon catheter. Stent 10 is formed from an absorbable material that is adapted to be absorbed in vivo after the lapse of two to three weeks. Of course material can be provided that dissolves over a longer period of time. In this regard, the ordinary artisan will readily appreciate from a review of this disclosure what known bioabsorbable materials could be utilized to form the stent of the present invention. The first embodiment of the stent is in the form of a mesh or "Chinese finger" cuff. Thus, prior to and during insertion into the body, the cuff can be in a collapsed or reduced diameter configuration (FIG. 1) and, after it has been delivered to the site of a lesion, it can be expanded to an enlarged diameter (as shown in FIG. 2) to support the vessel and retain the same in a dilated disposition.

To carry stent 10 to a region of a blood vessel to be treated, in accordance with a first embodiment of the present invention, stent 10 is first mounted in its collapsed condition to a balloon catheter 12 so as to be disposed about its collapsed distal balloon 14. Catheter 12 is then advanced with the aid of a guidewire 16, via the femoral artery, for example, to the site of the stenotic lesion and placed so that the stent and balloon are disposed within the constricted portion of the vessel. Balloon 14 is then inflated with a suitable fluid so as to expand stent 10 to a desired diameter wherein it abuts the vessel wall. Thus, plaque disposed on the vessel wall can be expanded at the time of stent delivery and concurrently therewith as opposed to prior to the delivery of the stent. This minimizes the requisite navigation of the vessels as well as the duration of the procedure as a whole.

After stent 10 has been expanded to the desired amount, balloon 14 is deflated and removed from the region of the lesion. In place, stent 10 will resist collapse of the vessel walls and yet, because the stent is formed from a relatively flexible and compliant material, it will not damage the vessel walls adjacent to the locus of the plaque and will thus avoid possible arterial rupture or aneurysm formation despite continuous stress from the beating of the heart. Furthermore, because the stent is formed as an open mesh configuration, it will be readily entrapped by endothelial overgrowth. This overgrowth will reinforce the vessel wall, decreasing the likelihood of subsequent collapse and yet, because it is absorbable, the stent will dissolve before undesirable, excessive encapsulation and hence undue wall thickening is effected. In addition, because of the encapsulation, the portions of the stent will not break off into the blood stream as it is dissolving. Thus the generation of emboli during the dissolution process is avoided and, because the stent will not be continuously exposed to blood within the vessel and the endothelial overgrowth forms a smooth inner vessel wall, the risk of thrombus formation is minimized.

Referring to FIGS. 3-4, the mesh-like absorbable stent 10 of the present invention is shown mounted on a mechanically expandable catheter 18. This catheter is used to carry stent 10 through the vascular system and place it within a coronary artery, for example, in the same manner as balloon catheter 12, discussed above. More particularly, the stent is mounted on the expandable distal end portion 20 of catheter 18 in its collapsed configuration. The catheter assembly is then guided with the aid of a guidewire 22 to the locus of an arterial obstruction. Once at an appropriate location, knob 24 provided on the proximal end of the catheter is rotated so that the expandable distal end portion 20 of the catheter is expanded by, for example, a shortening of the end portion 20 so that same increases in diameter. Consequently the diameter of stent 10 mounted on end portion 20 is increased. Again, the plaque disposed within the target vessel can be expanded either prior to the delivery of the stent or at the time that the stent is expanded. After stent 10 is in place, catheter knob 24 is again rotated but in an opposite direction so as to collapse the expandable portion of catheter 18 which can then be removed from the artery in question.

Figure 5:
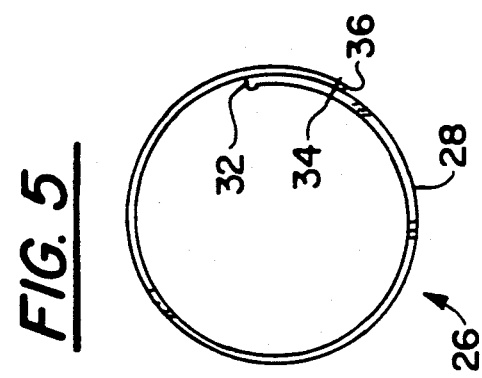
FIG. 5 is a perspective view of an alternative embodiment of an absorbable stent formed in accordance with the present invention.

Turning now to FIGS. 5 and 6, a second embodiment of an absorbable stent formed in accordance with the present invention is shown. In this embodiment, stent 26 is formed from a sheet of porous material 28, the porosity of the material being schematically illustrated in FIG. 6 as holes 30. The diameter of stent 26 is reduced by feeding one longitudinal edge 32 of the stent through a suitable longitudinal loop 34 provided on the other edge 36 of the stent. Thus, stent 26 can be reduced in diameter by a rolling motion while still having a cylindrical configuration on its outer surface for uniform engagement with a vessel wall. The "roll up" absorbable stent 26 is mounted on either a balloon catheter 12, a mechanically expandable catheter 18, or other suitable stent delivering assembly, as was the mesh-like stent 10 discussed in conjunction with FIGS. 1-4 above. The "roll up" stent 26 can then be delivered to a target location within, for example, a coronary artery. By expanding the distal balloon 14 of catheter 12 or the mechanically expandable distal end portion 20 of mechanically expandable catheter 18, stent 26 is expanded so as to engage the vessel wall. Preferably, this expansion simultaneously compresses the plaque disposed on the vessel wall.

After the stent has been carried to the desired stenotic region, expanded, and the dilating catheter removed, the endotheial tissue of the vessel rapidly encapsulates the stent by growth into and through the pores 30 defined in the stent material 28. Thus, after tissue encapsulation and over a period of two or three weeks or more, as desired, stent 26 will be absorbed by the body without the risk of generating emboli in the blood stream. Further, the encapsulating tissue growth forms a smooth interior wall for the vessel and reinforces the vessel wall against subsequent collapse but, because the stent dissolves, undue tissue growth and consequent hardening of the vessel wall is avoided.

While the invention has been described in connection with what is presently considered to be the most practical and preferred embodiments, it is to be understood that the invention is not to be limited to the disclosed embodiments, but, on the contrary, is intended to cover various modifications and equivalent arrangements included within the spirit and scope of the appended claims.

What is claimed is:

1. A vascular stent comprising:
 a tubular main body portion having a first open end and a second open end and a lumen extending therethrough, said main body portion being sized for transluminal placement within a coronary artery, said main body portion comprising a sheet of a bioabsorbable material having at least one of holes and pores defined therein for tissue ingrowth which has been rolled into a cylindrical configuration; said main body portion being expandable from a first reduced diameter allowing intravascular transport to a stenotic portion of a coronary artery to a second expanded diameter at said stenotic portion so as to engage and support the interior wall of the coronary artery in which it is disposed against collapse and restenosis, one longitudinal edge of said sheet including a means for receiving a second longitudinal end of said sheet so as to facilitate rolling of the sheet of material and maintaining same at a predetermined diameter prior to expansion thereof.

2. A vascular stent as in claim 1, in combination with a catheter assembly having a first end adapted to remain exterior to the vascular system and a second end adapted to be inserted into the coronary artery, said second end having an expandable end portion for carrying said main body portion into the coronary artery and for expanding said main body portion from said first reduced diameter to said second expanded diameter within a targeted portion of the coronary artery.

3. The combination of claim 2, further comprising means for mechanically expanding said catheter assembly second end by rotation of a knob provided on said catheter assembly first end.

4. The combination of claim 2, wherein said catheter assembly second end includes an inflatable balloon so as to provide said expansible end portion, whereby the main body portion can be expanded in diameter by inflating the balloon.

5. A method of preventing occlusion and restenosis after transluminal angioplasty comprising:

providing a catheter assembly having an expandable distal end portion;
 mounting an expandable vascular stent on said expansible distal end portion of said catheter assembly, said vascular stent including a tubular main body portion having a first open end and a second open end and a lumen extending therethrough, said main body portion being sized for transluminal placement within a coronary artery, said main body portion comprising a sheet of a bioabsorbable material having at least one of holes and pores defined therein for tissue ingrowth which has been rolled into a cylindrical configuration; said main body portion being expandable from a first reduced diameter allowing intravascular transport to a stenotic portion of a coronary artery to a second expanded diameter at said stenotic portion so as to engage and support the interior wall of the coronary artery in which it is disposed against collapse and restenosis, one longitudinal edge of said sheet including a means for receiving a second longitudinal end of said sheet so as to facilitate rolling of the sheet of material and maintaining same at a predetermined diameter prior to expansion thereof;
 inserting said catheter assembly distal end into a coronary artery;
 guiding said distal end to a targeted portion of a coronary artery;
 expanding said expandable portion so as to expand said vascular stent so as to engage, expand, and support the interior walls of the coronary artery;
 reducing the diameter of said distal end portion so as to leave said vascular stent in engagement with and supporting the coronary artery; and
 removing the distal end portion of the catheter assembly from the coronary artery.

6. The method as in claim 5, wherein said step of providing a catheter assembly comprises providing a catheter assembly having an inflatable balloon on the distal end thereof.

7. A method as in claim 5, wherein said step of providing a catheter assembly comprises providing a catheter asembly having a mechanically expandable distal end portion.

* * * * *